US00PP18551P2

(12) United States Plant Patent
Poindexter

(10) Patent No.: US PP18,551 P2
(45) Date of Patent: Mar. 4, 2008

(54) ***HEUCHERA* PLANT NAMED 'MIDNIGHT ROSE'**

(50) Latin Name: ***Heuchera* hybrid**
Varietal Denomination: Midnight Rose

(75) Inventor: Terri C. Poindexter, Lanham, MD (US)

(73) Assignee: Terra Nova Nurseries, Inc., Canby, OR (US)

( * ) Notice: Subject to any disclaimer, the term of this patent is extended or adjusted under 35 U.S.C. 154(b) by 21 days.

(21) Appl. No.: 11/542,919

(22) Filed: Oct. 3, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Klarquist Sparkman, LLP

(57) ABSTRACT

A new and distinct hybrid of *Heuchera* plant characterized by almost black colored leaves with pink spots that expand as the leaf grows larger. In summer the spots on the older leaves lighten to cream and pink.

2 Drawing Sheets

Botanical classification: *Heuchera* hybrid.
Variety denomination: 'Midnight Rose'.

The present invention relates to a new and distinct cultivar of *Heuchera* hybrid given the cultivar name of 'Midnight Rose'. *Heuchera* is in the family *Saxifragaceae. Heuchera* 'Midnight Rose' originated as a tissue culture mutation of *Heuchera* 'Obsidian'. It was found by the inventor in a shipment of *Heuchera* 'Obsidian' at Behnke Nurseries (700 Watkins Park Drive, Largo, Md. 20774).

This new and unique *Heuchera* is distinguished by:

1. Almost black colored leaves with pink spots that expand as the leaf grows larger.
2. In summer the spots on the older leaves lighten to cream and pink.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
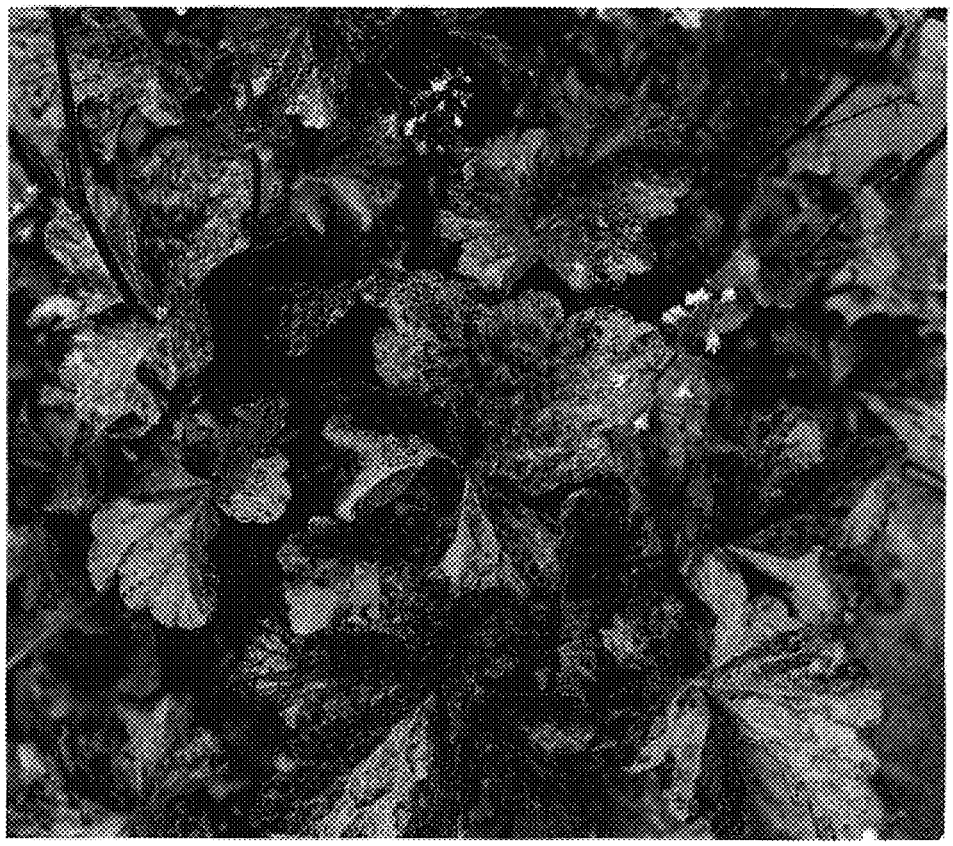
FIG. 1 shows *Heuchera* 'Midnight Rose' foliage and flowers growing in the ground in the trial beds in June in Canby, Oreg.
Figure 2:
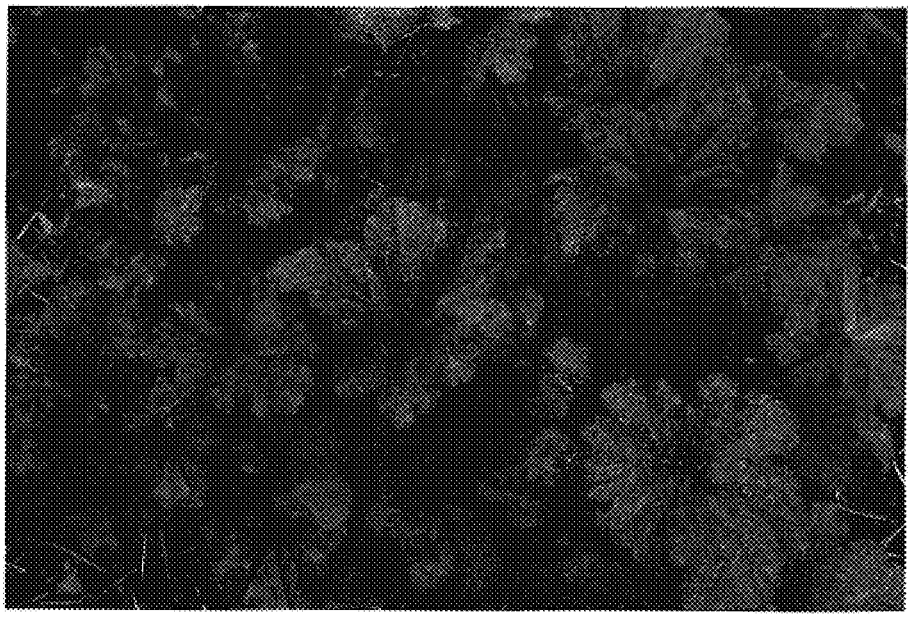
FIG. 2 shows *Heuchera* 'Midnight Rose' growing in the garden in April in Canby, Oreg.
Figure 3:
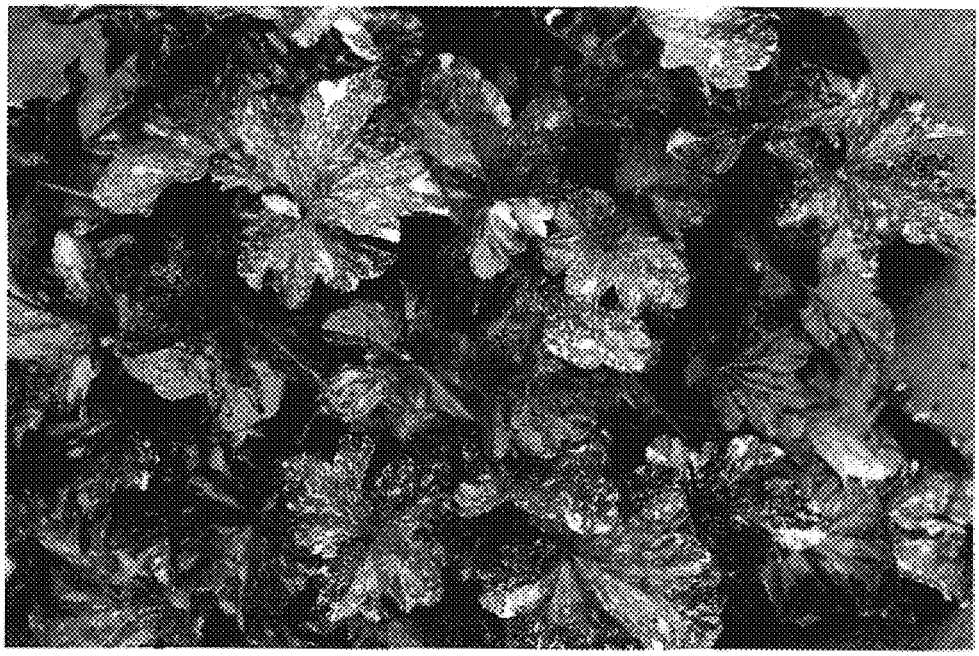
FIG. 3 shows *Heuchera* 'Midnight Rose' growing in the ground in the trial beds in mid July in Canby, Oreg.

The following is a detailed description of the new *Heuchera* hybrid based on observations of two year old specimen grown in the ground in Canby, Oreg. The color descriptions are all based on The Royal Horticultural Society Colour Chart.

Plant:
- *Form.*—Basal rosette, herbaceous perennial.
- *Hardiness.*—USDA Zone 4 to 9.
- *Size.*—30 cm tall from the ground to the top of the foliage and 35 cm wide.
- *Habit.*—Mounding.
- *Vigor.*—Excellent.
- *Roots.*—Fibrous, freely branching, fine, and white in color; roots develop easily from cuttings.

Leaf:
- *Type.*—Simple.
- *Arrangement.*—Rosette.
- *Shape.*—Orbicular to slightly ovate, cupping upward when plants are mature.
- *Lobing/division.*—7 rounded lobes, with 2 shallow secondary lobes on the terminal and longest lobe and 1 shallow secondary lobe on the lateral lobes.
- *Venation.*—Palmate.
- *Margins.*—Broadly crenate.
- *Apex.*—Mucronulate to obtuse.
- *Base.*—Cordate, lobes strongly overlapping.
- *Blade size.*—Grows to 9.5 cm long and 8.5 cm wide.
- *Surface texture.*—Sparsely puberulous on both sides.
- *Petiole length.*—Grows to 22 cm.
- *Petiole texture.*—Glandular puberulent.
- *Petiole color.*—Greyed Orange 177A and Greyed Purple 183A.
- *Leaf color.*—Topside — in spring Black 202A with pink spots Greyed Purple 186B; in summer the new leaves are Greyed Purple 187A to Brown 200A with the spots Greyed Purple 186B and the older leaves lighten to between Green 147A and Brown 200A with the spots lightening to Red 36A, Greyed Purple 186D, and Greyed Red 182D. Bottom side — Greyed Purple 187A with occasional patches of Greyed Purple 186B.

Inflorescence:

*Type.*—Thyrse.

*Number of flowers.*—About 100 per thyrse.

*Peduncle description.*—Unbranched, with 2 or 3 petiolate bracts per scape, bracts grow to 5 cm long and 4 cm wide, ovate, serrate, with 3 main lobes, peduncle grows to 74 cm tall and 5 mm wide, glandular puberulent, Greyed Purple 187A.

*Pedicel description.*—6 mm long and 1 mm wide, glandular puberulent, Greyed Purple 187A.

*Bloom period.*—May to July in Canby, Oreg.

Flower bud:

*Size.*—4 mm long, 2 mm wide.

*Description.*—Glandular puberulent, ovoid.

*Color.*—Greyed Purple 186A with Greyed Yellow 160A at tip.

Flower:

*Type.*—Perfect, zygomorphic.

*Shape.*—Campanulate.

*Size.*—6 mm long and 5 mm wide.

*Petal description.*—5, inconspicuous, 3 mm long and 1 mm wide, elliptic with a clawed base, entire, acute, White 155D and glandular on both sides.

*Calyx description.*—4 mm deep and 3 mm wide, urceolate, with 5 lobes divided ½ way to the base, broadly oblong with glandular hairs on both sides, entire, acute, Yellow Green 152A inside and on lobes inside and out, outside tube of calyx Brown 200A.

*Stamen.*—5, about 2 mm long, filaments Yellow White 158C, 1.2 mm long, anthers sterile, 0.8 mm long, Greyed Yellow 160D, no pollen.

*Pistil.*—4 mm long, Yellow Green 145A overall, ovary 2 mm long and 2 beaked style 2 mm long.

*Fragrance.*—None.

*Lastingness.*—Each thryse blooms for about 2 weeks on the plant.

Fruit:

*Type.*—Two-beaked ovoid capsule.

*Fertility.*—Low.

*Color.*—Tan. RHS 160C Greyed-Yellow to 199C Grey-Brown.

Seed:

*Shape.*—Linear.

*Size.*—2 mm. long.

*Color.*—Black RHS 202A.

Disease and pest tolerance: Excellent disease resistance to powdery mildew, the common problem of *Heuchera.* Susceptible to root weevils. Not highly susceptible to *Heuchera* rust.

COMPARISON TO SIMILAR *HEUCHERA*

Compared to *Heuchera* 'Obsidian', the parent plant, the new cultivar is the same except for the shocking pink spotting.

I claim:

1. A new and distinct hybrid of *Heuchera* plant substantially as shown and described.

* * * * *

UNITED STATES PATENT AND TRADEMARK OFFICE

CERTIFICATE OF CORRECTION

PATENT NO. : PP 18,551 P2
APPLICATION NO. : 11/542919
DATED : March 4, 2008
INVENTOR(S) : Terri C. Poindexter It is certified that error appears in the above-identified patent and that said Letters Patent is hereby corrected as shown below:

On the Title Page:

(73) Assignee, "Terra Nova Nurseries, Inc., Canby, OR (US)" should be --The Behnke Nurseries Co., Beltsville, MD (US)--.

Signed and Sealed this

Second Day of June, 2009

JOHN DOLL
*Acting Director of the United States Patent and Trademark Office*